United States Patent
Orth

(10) Patent No.: US 10,881,781 B1
(45) Date of Patent: Jan. 5, 2021

(54) BLOOD PROCESSING APPARATUS AND METHOD FOR DETOXIFYING BACTERIAL LIPOPOLYSACCHARIDE

(71) Applicant: ORTH CONSULTING, LLC, Maineville, OH (US)

(72) Inventor: Donald S. Orth, Cincinnati, OH (US)

(73) Assignee: ORTH CONSULTING, LLC, Maineville, OH (US)

( * ) Notice: Subject to any disclaimer, the term of this patent is extended or adjusted under 35 U.S.C. 154(b) by 0 days.

(21) Appl. No.: 16/862,378

(22) Filed: Apr. 29, 2020

(51) Int. Cl.
| | |
|---|---|
| *A61M 1/36* | (2006.01) |
| *A61M 1/26* | (2006.01) |
| *C12N 11/00* | (2006.01) |
| *B01J 31/00* | (2006.01) |

(52) U.S. Cl.
CPC .......... *A61M 1/3687* (2013.01); *A61M 1/267* (2014.02); *B01J 31/003* (2013.01); *C12N 11/00* (2013.01); *A61M 2205/3303* (2013.01); *A61M 2205/3368* (2013.01); *A61M 2205/36* (2013.01)

(58) Field of Classification Search
CPC ...... A61M 1/267; A61M 1/36; A61M 1/3607; A61M 1/3621; A61M 1/3679; A61M 1/3687; A61M 1/3689; A61M 2205/3303; A61M 2205/3368; A61M 2205/36; A61K 8/66; C12N 11/00; C12N 11/02; C12N 11/06; C12N 11/14; C12N 11/16; C12N 11/18; B01J 31/00; B01J 31/003
USPC .... 210/632, 645; 604/4.01, 5.01, 5.02, 5.03, 604/5.04; 435/269; 514/13.5, 15.3; 424/94.1, 94.2
See application file for complete search history.

(56) References Cited

U.S. PATENT DOCUMENTS

| | | | | |
|---|---|---|---|---|
| 4,378,435 | A | * | 3/1983 | Takagi ............... A61L 27/34 427/2.24 |
| 5,395,612 | A | | 3/1995 | Griffith |
| 5,437,861 | A | | 8/1995 | Okarma |
| 5,635,609 | A | * | 6/1997 | Levy ............... B01J 13/14 264/4.1 |
| 5,656,739 | A | * | 8/1997 | Cubicciotti ........... C07H 21/00 435/5 |

(Continued)

FOREIGN PATENT DOCUMENTS

| | | |
|---|---|---|
| WO | WO2017163087 A1 | 9/2017 |
| WO | WO2019175261 A1 | 9/2019 |

OTHER PUBLICATIONS

Karla Alejo Gonzalez et al, "Enzymatic detoxification of organophosphorus pesticides and related toxicants", Published in Journal of Pesticide Science, vol. 43, pp. 1-9, Jan. 31, 2018. (Year: 2018).*

(Continued)

*Primary Examiner* — Joseph W Drodge
(74) *Attorney, Agent, or Firm* — David R. Stevens; Stevens Law Group

(57) ABSTRACT

A detoxification method includes the steps of inducing flow of patient blood through an extracorporeal device inlet and outlet in fluid connection to the circulatory system of a patient. Biological agents including lipopolysaccharide (LPS) contained within patient blood can be detoxified by passing patient blood over a biochemical reactor surface having attached or immobilized *Saccharomyces boulardii* alkaline phosphatase enzyme, with the biochemical reactor being contained within the extracorporeal device.

18 Claims, 5 Drawing Sheets

(56) References Cited

U.S. PATENT DOCUMENTS

| | | | |
|---|---|---|---|
| 6,193,681 | B1 | 2/2001 | Davidner |
| 6,290,952 | B1 | 9/2001 | Poelstra |
| 7,556,768 | B2 | 7/2009 | Brady |
| 8,735,087 | B2 | 5/2014 | Brands |
| 10,258,734 | B2 | 4/2019 | Federspiel |
| 10,429,385 | B2 | 10/2019 | Winqvist |
| 10,435,457 | B2 | 10/2019 | Watters |
| 10,513,546 | B2 | 12/2019 | Watters |
| 2004/0014642 | A1* | 1/2004 | Nicolau .............. A61P 3/10 514/13.5 |
| 2004/0092491 | A1 | 5/2004 | Nieman |
| 2004/0185041 | A1 | 9/2004 | Walker |
| 2005/0249724 | A1 | 11/2005 | Lihme |
| 2010/0092467 | A1* | 4/2010 | Isenberg ............ B01J 37/0205 424/133.1 |
| 2011/0212053 | A1* | 9/2011 | Qian .................... A61P 3/00 424/85.2 |
| 2014/0166578 | A1 | 6/2014 | Ichim et al. |
| 2015/0166978 | A1* | 6/2015 | Cooney ............... A61M 1/3496 422/44 |
| 2017/0002481 | A1 | 1/2017 | Zussman et al. |
| 2019/0054227 | A1 | 2/2019 | Zheng |

OTHER PUBLICATIONS

Klaus Buttenschoen et al, "Endotoxin elimination in sepsis: physiology and therapeutic application", Published in Langenbecks Arch Surgery, vol. 395, pp. 597-605, Jun. 27, 2010. (Year: 2010).*

Margaret More et al, "*Saccharomyces boulardii* CNCM I-745 Improves Intestinal Enzyme Function: A Trophic Effects Review", Published in Clinical Medicine Insights: Gastroenterology, vol. 11, pp. 1-14, Published Dec. 17, 2017. (Year: 2017).*

Habja and Guttman, "Continuous-flow biochemical reactors: Biocatalysis, bioconversion, and bioanalytical applications using immobilized microfluidic enzyme reactors". J. Flow. Chem. 6(1):8-12, 2015.

Mohamad, et al. An overview of technologies for immobilization of enzymes and surface analysis techniques for immobilized enzymes. Biotech. Biotechnol. Equip. 29(2):205-220, 2015.

D.S. Orth. Insights into Cosmetic Microbiology. Allured Business Media, Carol Stream, IL. p. 224, 2010.

J. Behnsen and M. Raffatellu. Keeping the peace: Aryl hydrocarbon receptor signaling modulates the mucosal microbiota. Immunol. 39:206-207, 2013.

K. Poelstra et al. Dephosphorylation of endotoxin by alkaline phosphatase. Am. J. Pathol. 151(4):1163-1169, 1997.

J-P Buts et al. Saccharomyces boulardii produces in rat small intestine a novel protein phosphatase that inhibits Escherichia coli endotoxin by dephosphorylation. Pediatr Res 60(1):24-29, 2006.

K.M. Riggle et al. Intestinal alkaline phosphatase prevents the systemic inflammatory response associated with necrotizing enterocolitis. J. Surg. Res. 180(1):21-26 (2013).

S.M. Alam et al. Intestinal alkaline phosphatase prevents antibiotic-induced susceptibility to enteric pathogens. Ann Surg. 259(4):715-722 (2014).

M Estaki et al. Interplay between intestinal alkaline phosphatase, diet, gut microbes and immunity. World J Gastroenterol. 20(42):15650-15656 (2014).

J Fawley and D Gourlay. Intestinal alkaline phosphatase: A summary of its role in clinical disease. J Surg Res. 202(1):225-234 (2016).

A. Cauweis et al. Extracellular ATP drives systemic inflammation, tissue damage and mortality. Cell Death and Disease 5:e1102; doi:10.1038/cddis.2014.70. (2014).

R.M. Genta. The immunobiology of Helicobacter pylori gastritis. Seminars in R.M.• Gastrointestinal Disease. 8(1):2-11. PMID 9000497. (Jan. 1997).

N. Sharma, A.S. Akhade, and A. Qadri. Sphingosine-1-phosphate suppresses TLR-induced CXCL8 secretion from human T cells. Journal of Leukocyte Biology. 93(4):521-8. doi:10.1189/jlb. 0712328. PMID 23345392. (Apr. 2013).

A. Kathrani et al. "TLR5 risk-associated haplotype for canine inflammatory bowel disease confers hyper-responsiveness to flagellin". Plos One. 7(1):e30117. Bibcode:2012PLoSO . . . 730117K. doi:10. 1371/journal.pone.0030117. PMC 3261174. PMID 22279566. (2012).

S. Yoon. Structural basis of TLR5-flagellin recognition and signaling. Science 335:859-864, 2012.

K.T. T Chen et al. Identification of specific targets for the gut mucosal defense factor intestinal alkaline phosphatase. Am. J. Gastrointest. Liver Physiol. 299(2):G467- 475, 2010.

M.I. More and Y. Vandenplas. Saccharomyces boulardii CNCM I-745 improves intestinal enzyme function. Clin. Med. Insights. Gastroenterol. 11:1-14, 2018.

E.F. Gao, et al. Immobilization of alkaline phosphatase on solid surface through self- assembled monolayer and by active-site protection. J. Nanosci.Nanotechnol.14(6):4626-4631, 2014.

H. Ghiaci, et al. Enzyme immobilization: Part 2: Immobilization of alkaline phosphatase on Na-bentonite and modified bentonite. Applied Clay Science 43(3-4):308-316, 2009.

More et al., Saccharomyces boulardii CNCM I-745 Improves Intestinal Enzyme Function: A Trophic Effects Review, Clinical Medicine Insights: Gastroenterology, Feb. 2018.

* cited by examiner

BLOOD PROCESSING APPARATUS AND METHOD FOR DETOXIFYING BACTERIAL LIPOPOLYSACCHARIDE

FIELD OF THE INVENTION

This invention relates to detoxifying Gram negative bacterial lipopolysaccharide (LPS) and other inflammatory compounds in a person's blood. More particularly, an external biochemical reactor containing immobilized alkaline phosphatase enzymes for treating blood is described.

BACKGROUND OF THE INVENTION

There are hundreds of different species of bacteria in the gastrointestinal (GI) tract including both beneficial bacteria (i.e., the commensal microbiome) and potentially pathogenic bacteria. Gram negative bacteria are one major group of potentially pathogenic bacteria in the GI tract. Gram negative bacteria have a cell wall surrounded by an outer membrane composed of lipopolysaccharides (LPS). Harmful endotoxins can include lipoglycans and LPS, which are large molecules consisting of a lipid and a polysaccharide composed of O-antigen, an outer and inner protein core joined by a covalent bond, and a lipid A moiety joined to the inner core by phosphate groups. The endotoxins produced by different Gram negative bacteria differ in their antigenicity due to differences in the O-antigen, but they all have the same biological effects which are mainly due to lipid A. Lipid A contains two phosphate groups that are believed to be essential for its toxicity LPS in the bloodstream may be neutralized to some extent by many blood components including plasma lipids and proteins and LPS-binding protein (LPB). LPS binding to LPB elicits immune responses by presenting the LPS to cell surface pattern recognition receptors called CD14 and Toll-like receptors (e.g., TLR4) on macrophages, monocytes and endothelial cells. Interaction of LPS with these cellular receptors on monocytes and macrophages results in 1) production and release of cytokines including tumor necrosis factor alpha (TNFα), interleukins (e.g., IL-1, IL-6, IL-8) and platelet activating factor, resulting in activation of the arachidonic acid cascade to produce prostaglandins and leukotrienes, which are potent mediators of inflammation; 2) activation of the complement cascade C3 and C5a resulting in release of histamine which causes vasodilation, inflammation, and neutrophil chemotaxis; and 3) activation of the blood coagulation cascade that leads to acute disseminated intravascular coagulation, internal bleeding, hemorrhage and sepsis.

Sepsis is a life-threatening condition that develops when the body's response to infection causes injury to its own tissues and organs. Immediate, intensive treatment is crucial for surviving the condition and preventing septic shock because the risk of death from sepsis and septic shock increases with every passing hour. Toxic shock occurs when the body has an overwhelming response to infection—sometimes referred to as a "cytokine storm"—that causes the blood pressure to drop to dangerously low levels and triggers damaging changes to the organs causing them to become dysfunctional and stop working. Current treatment strategies include fluid replacement, antibiotics to control the infection, vasopressors to maintain adequate blood pressure, corticosteroids and anti-inflammatory drugs to lessen inflammation, and insulin to stabilize blood sugar levels. In some cases, a person might require surgery to remove abscesses and necrotic tissues that are a source of the microbial infection and toxins.

This disclosure describes a system, apparatus and method that can accomplish therapeutic removal of selected toxins within a biological system, including but not limited to those produced by Gram negative bacterial lipopolysaccharide (LPS) and other inflammatory compounds toxic to humans or animals.

BRIEF SUMMARY OF THE INVENTION

In one embodiment, a detoxification method includes the steps of inducing flow of patient blood through an extracorporeal device inlet and outlet in fluid connection to a circulatory system of a patient. Biological agents contained within patient blood can be detoxified by passing patient blood over a biochemical reactor surface having attached or immobilized alkaline phosphatase enzyme, with the biochemical reactor being contained within the extracorporeal device.

In one embodiment, the alkaline phosphatase further comprises *Saccharomyces boulardii* alkaline phosphatase.

In one embodiment, the alkaline phosphatase detoxifies Gram negative bacterial lipopolysaccharide (LPS).

In one embodiment, the alkaline phosphatase detoxifies at least one of Gram negative or Gram positive bacterial extracellular lipoteichoic acid, ATP, DNA, RNA or flagellin, yeast and fungal extracellular ATP, DNA and RNA, viral extracellular DNA and RNA, and host extracellular ATP, DNA, or RNA.

In one embodiment, the alkaline phosphatase detoxifies biological agents contained within patient blood by dephosphorylation.

In one embodiment, detoxifying biological agents using *S. boulardii* alkaline phosphatase is used to therapeutically treat at least one of sepsis, septic shock, inflammation, bacterermia, yeast infections, fungal infections, viral infections, systemic inflammatory response syndrome (SIRS), Gram negative bacterial lipopolysaccharide (LPS)-exacerbated conditions, IBD, IBS, Crohn's disease, ulcerative colitis, enterocolitis, NEC, menigitis, meningococcemia, trauma or hemorrhagic shock, burns, liver disease, pancreatitis, periodontal disease, pneumonia, cystic fibrosis, asthma, A1AT deficiency, COPD, pulmonary fibrosis, tuberculosis, coronary heart disease, congestive heart failure, renal disease, hemolytic uremic syndrome, kidney disease, autoimmune diseases including rheumatoid arthritis, systemic lupus erythematosus, cancer, Alzheimer's disease, diabetes, infections/abscess related diseases, and protein aggregation disorders including neurodegenerative diseases, Parkinson's disease, amyloidosis, and patients undergoing surgery, cardiovascular surgery, and transplants.

In one embodiment, alkaline phosphatase enzyme is immobilized by being covalently attached to the biochemical reactor surface.

In one embodiment, the biochemical reactor surface further comprises at least one of capillary tubing and microbeads.

In one embodiment, patient blood can be pumped through an extracorporeal device inlet and outlet in fluid connection to the circulatory system of a patient.

In one embodiment, the biochemical reactor surface is provided with a continuous blood flow from the patient that continues until the biological agent(s) being detoxified have been reduced to predetermined levels.

In one embodiment, a blood detoxification system includes an extracorporeal device having an inlet and outlet able to be placed in in fluid connection to the circulatory system of a patient. A biochemical reactor surface having attached alkaline phosphatase enzyme can act to detoxify biological agents contained within patient blood. The biochemical reactor can be contained within the extracorporeal device.

BRIEF DESCRIPTION OF THE DRAWINGS

Embodiments will be readily understood by the following detailed description in conjunction with the accompanying drawings.

DETAILED DESCRIPTION OF THE INVENTION

This disclosure may employ other terms and phrases not expressly defined herein. Such other terms and phrases shall have the meanings that they would possess within the context of this disclosure to those of ordinary skill in the art. In some instances, a term or phrase may be defined in the singular or plural. In such instances, it is understood that any term in the singular may include its plural counterpart and vice versa, unless expressly indicated to the contrary.

As used herein, the singular forms "a," "an," and "the" include plural referents unless the context clearly dictates otherwise. For example, reference to "a substituent" encompasses a single substituent as well as two or more substituents, and the like.

As used herein, the term "about", when used in reference to numerical ranges, cutoffs, or specific values, is used to indicate that the recited values may vary by up to as much as 10% from the listed value. As many of the numerical values used herein are experimentally determined, it should be understood by those skilled in the art that such determinations can, and often times, will vary among different experiments. The values used herein should not be considered unduly limiting by virtue of this inherent variation. The term "about" is used to encompass variations of this sort up to, or equaling, 10%.

The term "attach," "attached" or "attachment" as used herein, refers to connecting or uniting by a chemical bond, link, or force in order to keep two or more chemical compounds, polymers, proteins, polysaccharides, lipids, nucleic adds, or other biological or manufactured compositions together.

As used herein, "for example," "for instance," "such as," or "including" are meant to introduce examples that further clarify a more general subject matter. Unless otherwise expressly indicated, such examples are provided only as an aid for understanding embodiments illustrated in the present disclosure and are not meant to be limiting in any fashion. Nor do these phrases indicate any kind of preference for the disclosed embodiment.

Disclosed herein is an extracorporeal device, system or methods involving circulating, perfusing, or otherwise passing blood or other patient fluids through a system and device external to the body. One or more internal surfaces of the external or extracorporeal system include immobilized enzymatic agents to interact with one or more patient fluid borne biologic agents. The extracorporeal device, system or methods provide a platform that can be applied to numerous conditions and diseases involving circulating cells, compounds, or other biologic agents, such as those associated with bacterial, yeast, fungal, or viral infection, cell death, sepsis and many others.

Figure 1:
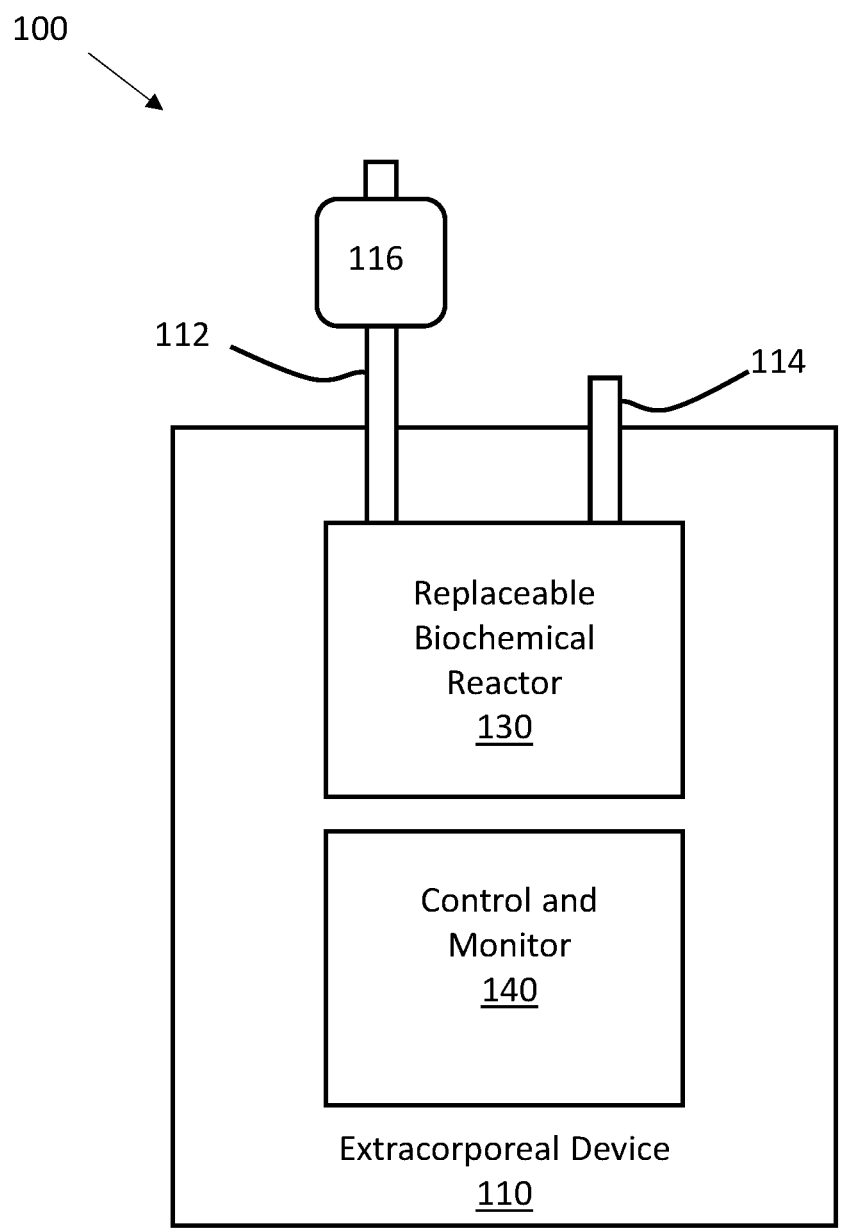
FIG. 1 illustrates a system including extracorporeal devices that can be attached to receive and detoxify blood or other fluids from a patient.

FIG. 1 illustrates a system 100 that can be attached to receive blood or other fluids from a human or animal patient. The system 100 includes an extracorporeal device 110 having an inlet 112 and outlet 114. Using a fluid pump 116, blood or other fluid is introduced and passed through a replaceable biochemical reactor 130. In some embodiments, the biochemical reactor 130 can form the entirety of the extracorporeal device 110. Surface attached and immobilized enzymatic agents in the biochemical reactor can remove toxins or other undesired contaminants and return the processed blood to the patient using outlet 114. A control and monitoring system 140 can be used to set fluid flow rates, maintain and monitor fluid temperature, and support sensors that can determine detoxification efficacy.

Figure 2:
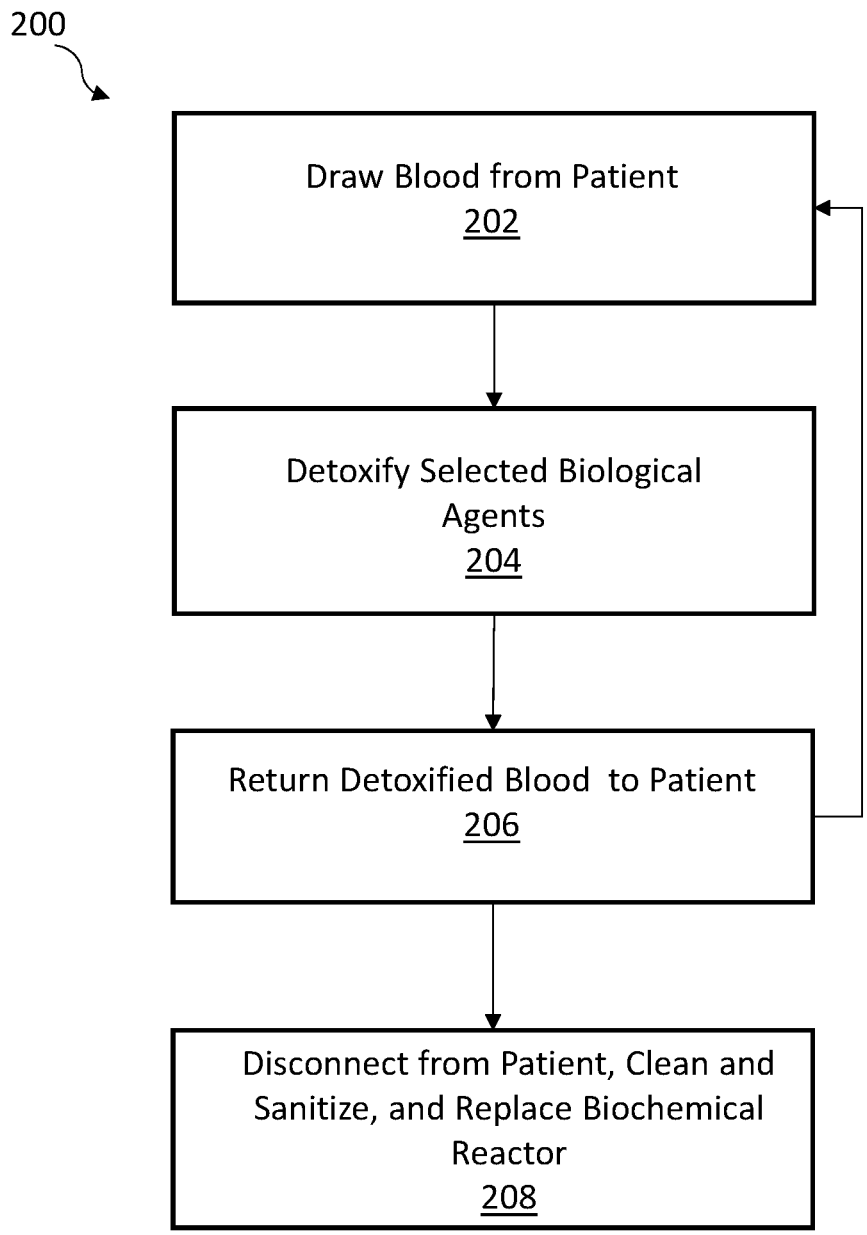
FIG. 2 illustrates one embodiment of a method for detoxifying patient blood.

FIG. 2 illustrates one embodiment of a method 200 for detoxifying human or animal patient blood. In a step 202, blood is drawn from a human or animal patient using a needle and suitable arterial or venous tap or puncture and transferred into an extracorporeal device. The patient blood is detoxified in step 204, and the process intermittently or continuously repeated until a significant volume of patient blood has been processed and returned to the patient (step 206). After detoxification, the patient can be disconnected, and the extracorporeal system cleaned. Cleaning can include sanitization or replacement of the biochemical reactor and readying the system for use by another patient.

In one embodiment of the device, system, or method of FIGS. 1 and 2, withdrawal of fluids from a human or animal patient can include blood drawn by venipuncture or arterial taps. Other bodily fluids such as cerebrospinal fluid, lymph fluid, urine, stomach and GI tract fluids can also be processed using the described systems and methods.

In one embodiment of the device, system, or method of FIGS. 1 and 2, the pump can include continuous, intermittent, or variable speed pumps. These can include but are not limited to peristaltic pump systems.

In one embodiment of the device, system, or method of FIGS. 1 and 2, the inlet and outlet can include luer locks or locking cannula systems.

In one embodiment of the device, system, or method of FIGS. 1 and 2, biochemical reactor can include fluid flow structures such as tubing, capillary tubes, hollow fibers, porous structures, and chambers containing unattached polymer or magnetic beads. Flow structures can be formed in whole or in part from glass, metal, ceramic, or polymeric materials. Fluid flow structures an be continuous, split into multiple separate flow channels using a manifold, or contain circulating closed chamber structures.

In one embodiment of the device, system, or method of FIGS. 1 and 2, immobilized enzymatic biologic agents can include alkaline phosphatase (AP), an enzyme with broad specificities that can catalyze dephosphorylation of DNA, RNA, ribo- and deoxyribonucleoside triphosphates in humans. For example, alkaline phosphatase can enzymatically react with adenosine triphosphate to yield adenosine diphosphate and a free phosphate. Under biological conditions, alkaline phosphatase can remove phosphate from phosphate containing biologic agents such as nucleotides and proteins, inactivating or detoxifying the biologic agents.

Various types or isozymes of alkaline phosphatase can be used, including but not limited to human or animal derived intestinal AP (IAP), tissue-nonspecific AP (ALPL), placental AP (ALPP), germ cell AP (GCAP), or yeast derived alkaline phosphatase. Because of wide availability, ease of culture, and long duration of enzymatic activity, alkaline phosphatase produced by strains of the yeast *Saccharomyces cerevisiae* var. *boulardii* (*S. boulardii*) can be used in one embodiment. Advantageously, *S. boulardii* alkaline phosphatase has excellent stability and active lifetime, a pH activity profile suited for dephosphorylating toxins at normal pH blood, is less expensive to prepare than human or animal sources of alkaline phosphatase, and man-made alkaline phosphatase such as that made using recombinant DNA technology In one embodiment of the device, system, or method of FIGS. 1 and 2, attachment of enzymatic biologic agents such as alkaline phosphatase (AP) can include linkage using conventional affinity tag binding, attachment or adsorption on glass, beads, alginate structures or other matrix, entrapment in insoluble beads or microspheres, enzymatic cross linkage to create an enzymatically reactive surface, or covalent bonding. Covalent bonding can be random or site specific. Amino, thiol, carboxyl, or cyanogen bromide activation can be used. In some embodiments, discrete linking agents that are attached between the alkaline phosphatase and a surface can be used. In some embodiments, surfaces can be chemically modified to allow enzyme attachment, or functional groups exposed on the surface can be activated. Covalent or ionic coupling of a linking agent or enzyme to the surface can include linking of one or more functional groups on the surface or the enzyme.

In one embodiment of the device, system, or method of FIGS. 1 and 2 biologic agents or compounds that interact with the immobilized enzymatic agents can include blood or fluid conveyed LPS, as well as adenosine triphosphate (ATP), DNA, RNA and flagellin. More specifically, in other embodiments, at least one of Gram negative or Gram positive bacterial extracellular lipoteichoic acid, ATP, DNA, RNA or flagellin, yeast and fungal extracellular ATP, DNA and RNA, viral extracellular DNA and RNA, and host extracellular ATP, DNA, or RNA can be detoxified after interaction with immobilized alkaline phosphatase.

In one embodiment of the device, system, or method of FIGS. 1 and 2, treatable diseases, conditions, or symptoms of humans or animals can include but are not limited to:

1) Stand-alone treatment or in conjunction with other treatment strategies for bacteremia, sepsis and septic shock including oral dosing and IV injection of IAP or other AP isozymes;

2) Treatment to lessen morbidity due to LPS translocating from the gastrointestinal tract into the bloodstream when the intestinal permeability barrier becomes compromised due to dysbiosis caused by Gram negative bacterial infection and/or other acute or chronic metabolic disorders such as IBD, inflammatory bowel syndrome (IBS), Crohn's disease, cancer, liver disease, autoimmune diseases, diabetes, or aging;

3) Treatment to detoxify LPS exogenous ATP, DNA and flagellin in the bloodstream due to translocation across the intestinal barrier or due to microbial infections, bacteremia, abscesses or tissue necrosis at any site in the body;

4) Treatment to detoxify LPS exogenous ATP, DNA and flagellin in the bloodstream due to translocation following antibiotic treatment that afters the gut microbiome and disrupts homeostasis to allow increased contact of Gram negative bacteria in the intestinal lumen to gain access to Toll-like receptors on enterocytes, resulting in inflammation and decreased intestinal barrier function. In some situations, *S. boulardii* probiotics and/or oral IAP can additionally be used to accelerate return to normal homeostasis in the gastrointestinal tract;

5) Treatment to reduce the inflammatory response associated with necrotizing enterocolitis (NEC) and mitigate the septic response and end-organ injury;

6) Treatment of sepsis, septic shock, inflammation, bacteremia, yeast infections, fungal infections, viral infections, systemic inflammatory response syndrome (SIRS), Gram negative bacterial lipopolysaccharide (LPS)-exacerbated conditions, IBD, IBS, Crohn's disease, ulcerative colitis, enterocolitis, NEC, meningitis, meningococcenlia, trauma or hemorrhagic shock, burns, liver disease, pancreatitis, periodontal disease, pneumonia, cystic fibrosis, asthma, A1AT deficiency, COPD, pulmonary fibrosis, tuberculosis, coronary heart disease, congestive heart failure, renal disease, hemolytic uremic syndrome, kidney disease, autoimmune diseases including rheumatoid arthritis, systemic lupus erythematosus, mast cell activation disorders, cancer, Alzheimer's disease, diabetes, infections/abscess related diseases, and protein aggregation disorders including neurodegenerative diseases, Parkinson's disease, amyloidosis, and patients undergoing surgery, cardiovascular surgery, and transplants;

7) Treatment of conditions associated with extracellular ATP, including hypoxia and ischemia that result in active release from cells and passive leakage from damaged/dying cells, and downregulation of ectonucleotidases. Examples include but are not limited to SIRS, MAT, COPD, IBD, IBS, diverticulosis, and diverticulitis;

8) Treatment of proinflammatory conditions derived from increased ATP, DNA and flagellin in patients with IBD, ulcerative colitis, or other disorder in which there is a decreased expression of IAP that results in excessive levels of proinflammatory compounds in the bloodstream;

9) Treatment to reduce levels of LPS, DNA, extracellular ATP and flagellin in the bloodstream that may be elevated following a course of systemic antibiotic treatment that altered the GI microbiome to favor non-commensal Gram negative bacteria including *Escherichia coli, Citrobacter freundii, Enterobacter aerogenes*, and other bacteria, resulting in increased translocation of LPS, DNA, external ATP and flagellin into the bloodstream. Reduction of these toxins in the bloodstream can reduce immunological response and enable the body to re-establish the normal commensal microflora and homeostasis in the Gi tract; and 10) Treatment to reduce toxicity of LPS and microbial or host chemical compounds that may be proinflammatory including lipoteichoic acid, ATP, DNA and flagellin to reduce patient morbidity and result in fewer finger, hand, toe, foot, arm and leg amputations and surgery caused by sepsis and inflammation.

Figure 3:
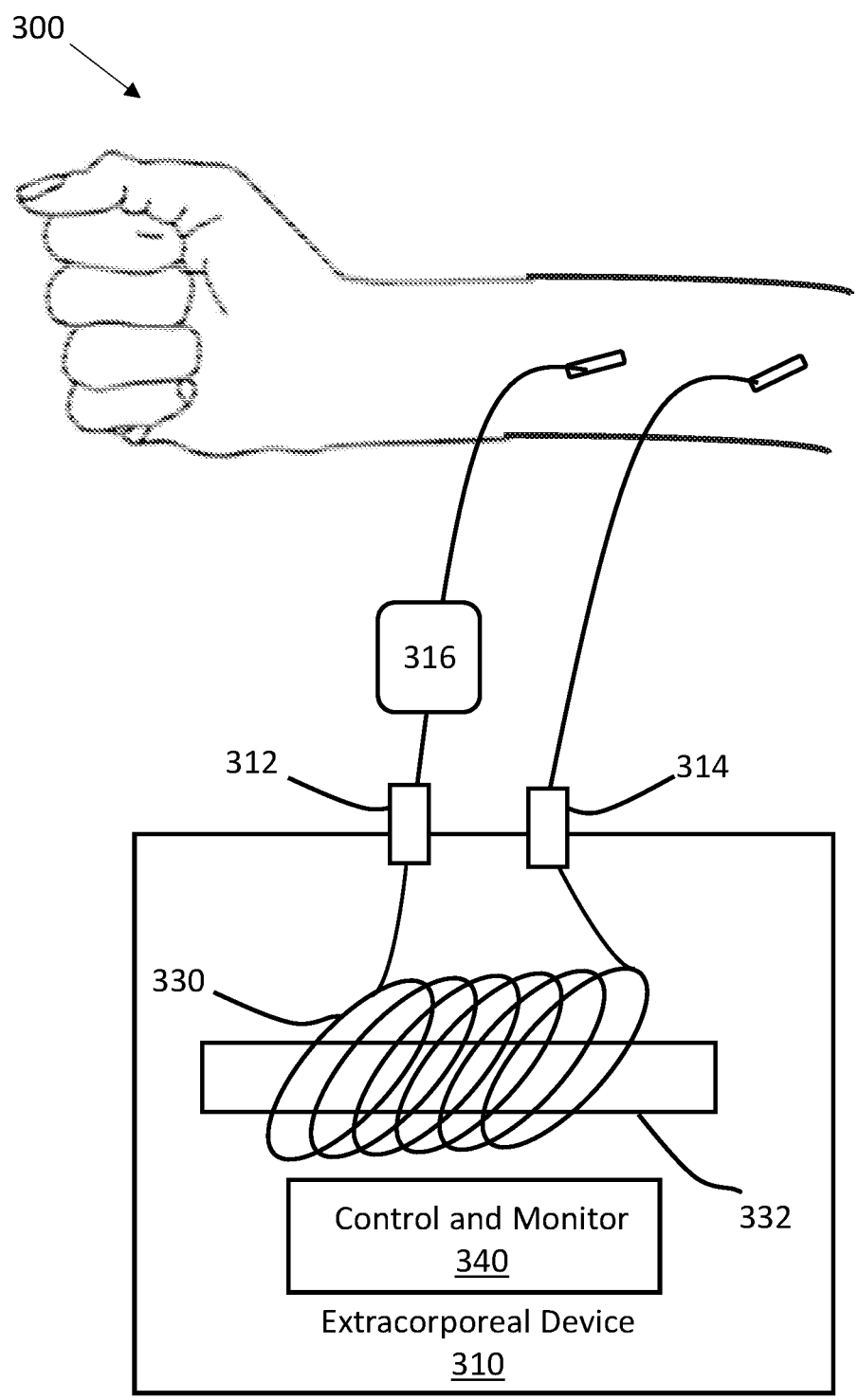
FIG. 3 illustrates one embodiment of an extracorporeal devices that can be attached to receive and detoxify blood that includes coiled tubing supporting immobilized enzymes.

FIG. 3 illustrates one embodiment of an extracorporeal device that can be attached to receive and detoxify blood that includes coiled tubing supporting immobilized enzymes. As seen in FIG. 3, a system 300 can be attached to receive blood from vein connections to a patient's arm. The system 300 includes an extracorporeal device 310 having a luer lock inlet 312 and luer lock outlet 314. Using a fluid pump 316, blood or other fluid is introduced and passed through a replaceable biochemical reactor 330 that includes coiled or otherwise compactified tubing. Surface attached and immobilized enzymatic agents in the biochemical reactor can remove toxins or other undesired contaminants and return the processed blood to the patient using outlet 314. A control and monitoring system 340 can be used to set fluid flow rates, maintain and monitor fluid temperature, and support sensors that can determine detoxification efficacy. In this embodiment, a heater element 332 can be connected to the control and monitor device to maintain blood temperature at about 37 degrees Celsius for human patients, or normal blood temperature for non-human patients.

Figure 4:
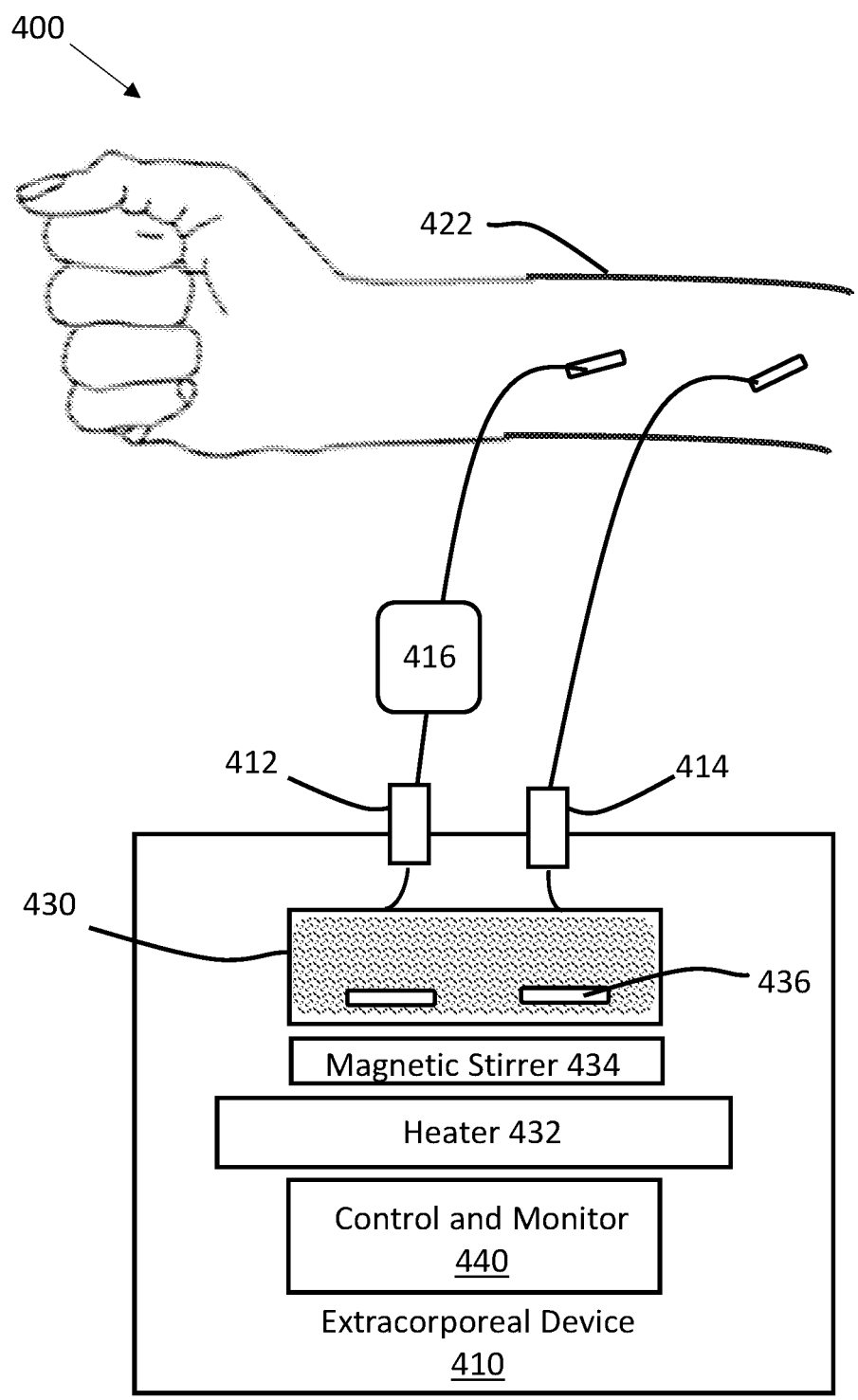
FIG. 4 illustrates one embodiment of an extracorporeal device that can be attached to receive and detoxify blood that includes a flow chamber supporting beads with immobilized enzymes.

FIG. 4 illustrates one embodiment of an extracorporeal device that can be attached to receive and detoxify blood that includes a flow chamber supporting beads with immobilized enzymes. As seen in FIG. 4, a system 400 can be attached to receive blood or other fluids from arteries or vein connections to a patient's arm. The system 400 includes an extracorporeal device 410 having a luer lock inlet 412 and luer lock outlet 414. Using a fluid pump 416, blood or other fluid is introduced and passed through a replaceable biochemical reactor 430 that includes a fluid chamber partially filled with beads capable of surface attachment with immobilized enzymatic agents. A magnetic stirring system 434 can be used to rotate magnetic cylinders 436 within the replaceable biochemical reactor 430. Surface attached and immobilized enzymatic agents in the biochemical reactor can remove toxins or other undesired contaminants and return the processed blood to the patient using outlet 414. A control and monitoring system 440 can be used to set fluid flow rates, maintain and monitor fluid temperature, and support sensors that can determine detoxification efficacy. In this embodiment, a heater element 432 can be connected to the control and monitor device to maintain blood temperature at a desired set point.

Figure 5:
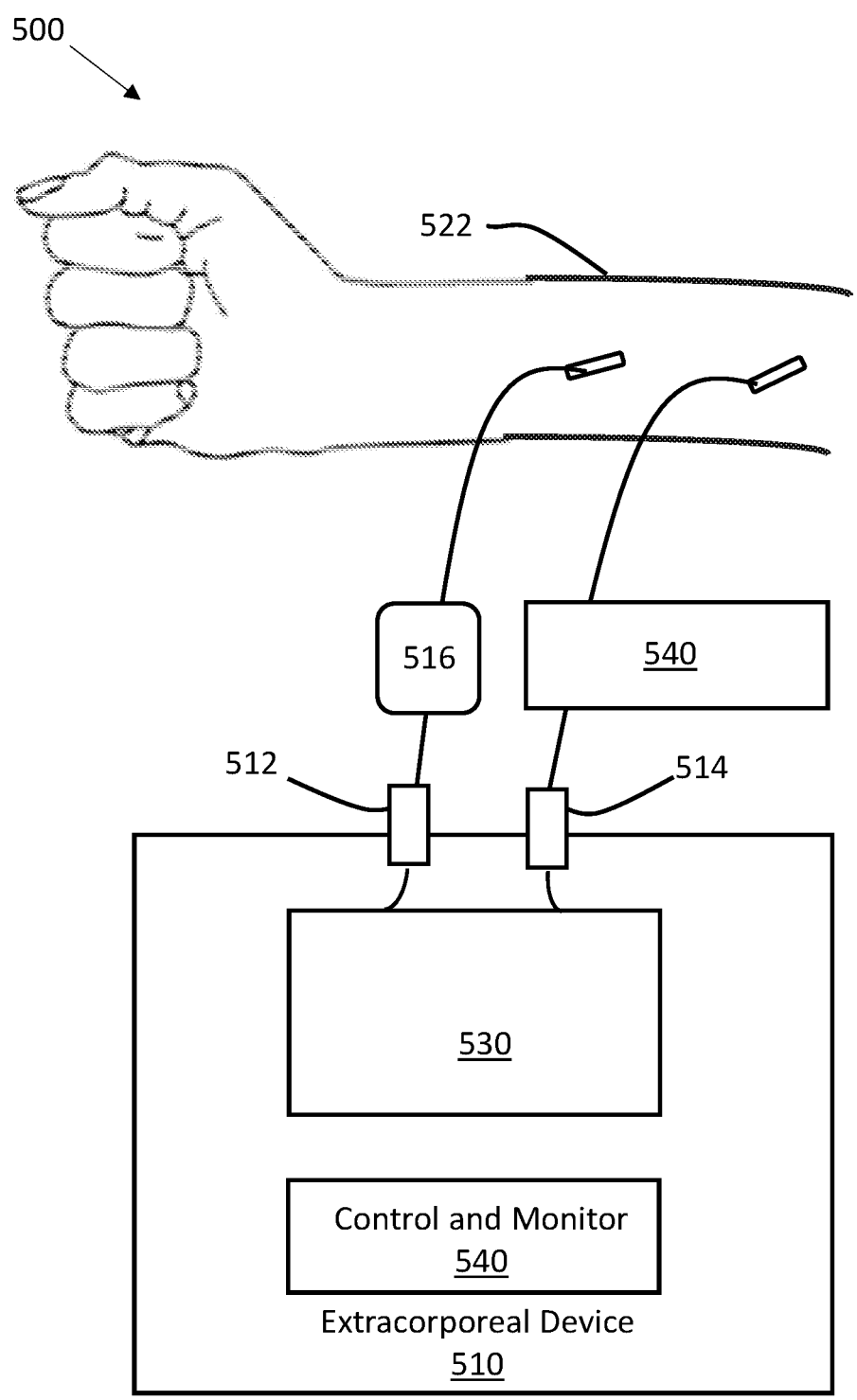
FIG. 5 illustrates one embodiment of an extracorporeal device that can be attached to receive and detoxify blood that is further connected to other diagnostic or therapeutic equipment.

FIG. 5 illustrates one embodiment of an extracorporeal device that can be attached to receive and detoxify blood that is further connected to other diagnostic or therapeutic equipment. As seen in FIG. 5, a system 500 can be attached to receive blood or other fluids from arteries or vein connections to a patient's arm. The system 500 includes an extracorporeal device 510 having a luer lock inlet 512 and luer lock outlet 514. Using a fluid pump 516, blood or other fluid is introduced and passed through a replaceable biochemical reactor 530 that includes immobilized enzymatic agents such as alkaline phosphatase. After passing through the biochemical reactor 530, blood can be further processed by separate (as shown) or built-in diagnostic or therapeutic systems 540. Diagnostic systems can include inline assays for free phosphate, real-time flow cytometry, or other blood health diagnostics. Therapeutic systems can include additional hemoperfusion, hemofiltration, oxygenation, or other blood processing methods. In some embodiments, diagnostic or therapeutic systems 540 can include in-line sampling ports that permit periodic sample taking.

As will be appreciated, the described systems and methods of FIGS. 3, 4, and 5 that are applicable to venous blood taken and returned to a patient arm can be adapted to process fluids from other body sites. Such bodily fluids may be routed to the extracorporeal device for detoxification and then returned to the body.

Example 1

In one example embodiment, a sterile hypodermic needle set can be used for accessing a patient's vein, (e.g., Blood Collection Set, Vaculet 21Gx¾" Winged, w/Multi-Sample Adapter, 12" Tubing, or similar vein accessing device with a larger bore needle, if needed). A 36" length of sterile plastic tubing can be used to pass through a peristaltic pump and connect the Vaculet with the biochemical reactor with a luer lock. The peristaltic pump or similar pumping device can be used for pumping blood from the patients arm to the biochemical reactor.

An external continuous-flow biochemical reactor is prepared by immobilizing *S. boulardii* alkaline phosphatase (SBAP) on the inner surface of polystyrene, polymethacrylate, or other plastic capillary tubing as described by Habja and Guttman "Continuous-flow biochemical reactors: Biocatalysis, bioconversion, and bioanalytical applications using immobilized microfluidic enzyme reactors". J. Flow. Chem. 6(1):8-12, 2015, or Mohamad, et al. "An overview of technologies for immobilization of enzymes and surface analysis techniques for immobilized enzymes. Biotech. Biotechnol. Equip. 29(2):205-220, 2015. Enough capillary tubing (i.e., preferably up to 36 inches long) is used to allow immobilization of 50-1,500 IU AP, and preferably 200-500 IU SBAP in the tubing, which becomes the biochemical reactor. The plastic tubing with immobilized SBAP on the inner surface is sterilized and may be stored in the refrigerator at 4° C. for several months prior to use. When ready for use, the plastic tubing is placed into a 12"×12"×12" chamber that has a lid that opens for placement of the tubing inside, a side opening with a luer lock for connection to the plastic tubing from the patient's arm (by way of the peristaltic pump), and a second side opening with a luer lock for connecting to the line that returns blood to the patient. Alternatively, the plastic tubing can be used without insertion into a chamber, with the pump and tubing together forming a portion of the extracorporeal device by themselves. The continuous-flow biochemical reactor can dephosphorylate approximately 50% of the LPS, external ATP, DNA and flagellin in blood per passage through it as the blood is pumped slowly (e.g., flow rate of 0.5-50 mL/min, and typically up to 10 mL/min) through the capillary tubing before returning it to the patient. Passage of the patient's blood through the biochemical reactor dephosphorylates and thereby detoxifies LPS, Gram negative or Gram positive bacterial extracellular ATP, DNA, RNA and flagellin, and host extracellular ATP, DNA, and RNA in the patient's blood before it is returned to the patient Example 2

A sterile hypodermic needle set can be used for accessing a patient's vein and a peristaltic pump can be used for pumping blood from the patients arm to a biochemical reactor. An external continuous-flow biochemical reactor is prepared by use of a sterile 250 mL closed container with a magnetic stirring bar that contains 10-150 g, and preferably 50 g of microbeads with immobilized SBAP, prepared by covalent bonding to have 50-1,500 IU SBAP, and preferably 200-500 IU SBAP prepared aseptically in the biochemical reactor. The external continuous-flow biochemical reactor has inlet and outlet connections for connecting with blood being pumped to and from the continuous-flow biochemical reactor. The container with SBAP covalently immobilized on the plastic beads is sterilized and may be stored in the refrigerator at 4° C. for several months prior to use. When ready for use, the container is placed onto a magnetic stirrer and stirring is started when blood begins to fill the container. A length of sterile plastic tubing is used to connect the biochemical reactor to the patient's arm vein for returning treated blood to the patient's arm or leg vein.

The peristaltic pump may be turned on after checking to ensure that all connections are tight so that they will not leak or allow the blood to become contaminated, and the pump is run continuously. Passage of the patient's blood through the biochemical reactor dephosphorylates and thereby detoxifies LPS, Gram negative or Gram positive bacterial extracellular lipoteichoic acid, ATP, DNA, RNA and flagellin, and host extracellular ATP, DNA, and RNA in the patient's blood before it is returned to the patient.

The biochemical reactor chamber is maintained at approximately body temperature (37° C.) by use of a thermostatically-controlled heating device. The patient's blood is pumped continuously through the biochemical reactor until analytical testing shows that levels of the LPS and inflammatory chemicals including, but not limited to ATP, DNA and flagellin, and/or selected markers (e.g., cytokines including TNFα, IL-6, or IL-8) have been reduced to undetectable or baseline levels and the patient's signs have returned to normal.

While specific embodiments have been illustrated and described above, it is to be understood that the disclosure provided is not limited to the precise configuration, steps, and components disclosed. Various modifications, changes, and variations apparent to those of skill in the art may be made in the arrangement, operation, and details of the methods and systems disclosed, with the aid of the present disclosure.

Without further elaboration, it is believed that one skilled in the art can use the preceding description to utilize the present disclosure to its fullest extent. The examples and embodiments disclosed herein are to be construed as merely illustrative and exemplary and not a limitation of the scope of the present disclosure in any way. It will be apparent to those having skill in the art that changes may be made to the details of the above-described embodiments without departing from the underlying principles of the disclosure herein.

The invention claimed is:

1. A detoxification method, comprising:
   inducing flow of blood of a patient through an extracorporeal device inlet and outlet in fluid connection to a circulatory system of the patient; and
   detoxifying biological agents contained within the blood of the patient by passing the blood of the patient over a biochemical reactor surface having attached alkaline phosphatase enzyme, with the biochemical reactor being contained within the extracorporeal device;
   wherein the alkaline phosphatase enzyme comprises S. boulardii alkaline phosphatase.

2. The detoxification method of claim 1, wherein the alkaline phosphatase enzyme detoxifies Gram negative bacterial lipopolysaccharide (LPS) in the blood of the patient.

3. The detoxification method of claim 1, wherein the alkaline phosphatase enzyme detoxifies a substance in the blood of the patient selected from the group consisting of:
   Gram negative or Gram positive bacterial extracellular lipoteichoic acid;
   any of bacterial ATP, DNA, RNA or flagellin;
   any of yeast extracellular ATP, DNA or RNA;
   any of fungal extracellular ATP, DNA or RNA;
   any of viral extracellular DNA or RNA; and
   any of host extracellular ATP, DNA, or RNA.

4. The detoxification method of claim 1, wherein the alkaline phosphatase enzyme detoxifies biological agents contained within the blood of the patient by dephosphorylation.

5. The detoxification method of claim 1, wherein the method is used to therapeutically treat any of sepsis, septic shock, inflammation, bacteremia, yeast infections, fungal infections, viral infections, systemic inflammatory response syndrome (SIRS), Gram negative bacterial lipopolysaccharide (LPS) in a bloodstream of the patient, IBD, IBS, Crohn's disease, ulcerative colitis, enterocolitis, NEC, meningitis, meningococcemia, trauma, hemorrhagic shock, burns, liver disease, pancreatitis, periodontal disease, pneumonia, cystic fibrosis, asthma, A1AT deficiency, COPD, pulmonary fibrosis, tuberculosis, coronary heart disease, congestive heart failure, renal disease, hemolytic uremic syndrome, kidney disease, autoimmune diseases including rheumatoid arthritis, systemic lupus erythematosus, mast cell activation disorders, cancer, Alzheimer's disease, diabetes, infection resulting in LPS or lipoteichoic acid in the bloodstream of the patient, abscess resulting in LPS or lipoteichoic acid in the bloodstream of the patient, protein aggregation disorders including neurodegenerative diseases, Parkinson's disease, and amyloidosis of the patient or the patient while undergoing surgery.

6. The detoxification method of claim 1, wherein the alkaline phosphatase enzyme is covalently attached to the biochemical reactor surface.

7. The detoxification method of claim 1, wherein the biochemical reactor surface further comprises at least one of capillary tubing and microbeads.

8. The detoxification method of claim 1, further comprising the step of pumping the blood of the patient through the extracorporeal device inlet and outlet in fluid connection to the circulatory system of the patient.

9. The detoxification method of claim 1, wherein the biochemical reactor surface is provided with a continuous flow of the blood of the patient from the patient that continues until the biological agents being detoxified have been reduced to predetermined levels.

10. A blood detoxification system, comprising:
    an extracorporeal device having an inlet and outlet able to be placed in fluid connection to a circulatory system of a patient; and
    a biochemical reactor surface having attached alkaline phosphatase enzyme, with the biochemical reactor being contained within the extracorporeal device and acting to detoxify biological agents contained within blood of the patient;
    wherein the alkaline phosphatase comprises S. boulardii alkaline phosphatase.

11. The blood detoxification system of claim 10, wherein the alkaline phosphatase detoxifies Gram negative bacterial lipopolysaccharide (LPS) in the blood of the patient.

12. The blood detoxification system of claim 10, wherein the alkaline phosphatase detoxifies a substance in the blood of the patient selected from the group consisting of:
    Gram negative or Gram positive bacterial extracellular lipoteichoic acid;
    any of bacterial ATP, DNA, RNA or flagellin;
    any of yeast extracellular ATP, DNA or RNA;
    any of fungal extracellular ATP, DNA or RNA;
    any of viral extracellular DNA or RNA; and
    any of host extracellular ATP, DNA, or RNA.

13. The blood detoxification system of claim 10, wherein the alkaline phosphatase detoxifies biological agents contained within the blood of the patient by dephosphorylation.

14. The blood detoxification system of claim 10, wherein the system is operable to therapeutically treat any of sepsis, septic shock, inflammation, bacteremia, yeast infections, fungal infections, viral infections, systemic inflammatory response syndrome (SIRS), Gram negative bacterial lipopolysaccharide (LPS) in the blood of the patient, IBD, IBS, Crohn's disease, ulcerative colitis, enterocolitis, NEC, meningitis, meningococcemia, trauma, hemorrhagic shock, burns, liver disease, pancreatitis, periodontal disease, pneumonia, cystic fibrosis, asthma, A1AT deficiency, COPD, pulmonary fibrosis, tuberculosis, coronary heart disease, congestive heart failure, renal disease, hemolytic uremic syndrome, kidney disease, autoimmune diseases including rheumatoid arthritis, systemic lupus erythematosus, mast cell activation disorders, cancer, Alzheimer's disease, diabetes, infections resulting in LPS or lipoteichoic acid in a bloodstream of the patient; abscess resulting in LPS or lipoteichoic acid in a bloodstream of the patient, and protein aggregation disorders including neurodegenerative diseases, Parkinson's disease, and amyloidosis of the patient or the patient, while undergoing surgery.

15. The blood detoxification system of claim 10, wherein the alkaline phosphatase enzyme is covalently attached to the biochemical reactor surface.

16. The blood detoxification system of claim 10, wherein the biochemical reactor surface further comprises at least one of capillary tubing and microbeads.

17. The blood detoxification system of claim 10, further comprising a pump arranged to pump the blood of the patient through the extracorporeal device inlet and outlet in fluid connection to the circulatory system of the patient.

18. The blood detoxification system of claim 10, wherein the biochemical reactor surface arranged to receive a continuous blood flow from the patient that continues until the biological agents being detoxified have been reduced to predetermined levels.

* * * * *

UNITED STATES PATENT AND TRADEMARK OFFICE
CERTIFICATE OF CORRECTION

PATENT NO. : 10,881,781 B1
APPLICATION NO. : 16/862378
DATED : January 5, 2021
INVENTOR(S) : Donald S. Orth It is certified that error appears in the above-identified patent and that said Letters Patent is hereby corrected as shown below:

In the Specification

Under BRIEF SUMMARY OF THE INVENTION:

In Column 2, Line 41, the word "menigitis" should be corrected to "meningitis."

Under DETAILED DESCRIPTION OF THE INVENTION:

In Column 3, Line 62, the word "adds" should be corrected to "acids."

In Column 4, Line 62, the word "an" should be corrected to "can."

In Column 6, Line 5, the word "afters" should be corrected to "alters."

In Column 6, Line 21, the word "meningococcenlia" should be corrected to "meningococcemia."

In Column 6, Line 38, the word "MAT" should be corrected to "A1AT."

Signed and Sealed this
Twenty-seventh Day of July, 2021

Drew Hirshfeld
*Performing the Functions and Duties of the
Under Secretary of Commerce for Intellectual Property and
Director of the United States Patent and Trademark Office*